United States Patent
Henderson et al.

(10) Patent No.: US 11,639,921 B2
(45) Date of Patent: May 2, 2023

(54) OIL API DETERMINATION OF RESERVOIR ROCKS BY OXIDATION

(71) Applicant: SAUDI ARABIAN OIL COMPANY, Dhahran (SA)

(72) Inventors: Sebastian Robert Glynn Henderson, Dhahran (SA); Sedat Inan, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 113 days.

(21) Appl. No.: 17/377,025

(22) Filed: Jul. 15, 2021

(65) Prior Publication Data

US 2023/0015799 A1    Jan. 19, 2023

(51) Int. Cl.
- G01N 33/28    (2006.01)
- G01N 9/36    (2006.01)
- G01N 21/3504    (2014.01)

(52) U.S. Cl.
CPC .......... *G01N 33/2823* (2013.01); *G01N 9/36* (2013.01); *G01N 21/3504* (2013.01)

(58) Field of Classification Search
CPC ... G01N 33/2823; G01N 9/36; G01N 21/3504
See application file for complete search history.

(56) References Cited

U.S. PATENT DOCUMENTS

| | | |
|---|---|---|
| 4,120,659 A | 10/1978 | Cropper |
| 4,248,599 A | 2/1981 | Mommessin et al. |
| 5,866,814 A | 2/1999 | Jones et al. |
| 10,088,465 B2 * | 10/2018 | Pillot ............... G01N 33/241 |

(Continued)

FOREIGN PATENT DOCUMENTS

| | | |
|---|---|---|
| CN | 102207491 A | 10/2011 |
| CN | 108362758 A | 8/2018 |

(Continued)

OTHER PUBLICATIONS

English translation of CN112903900 accessed from iq.ip.com Dec. 14, 2022.*

(Continued)

*Primary Examiner* — David Z Huang
*Assistant Examiner* — Jean F Morello
(74) *Attorney, Agent, or Firm* — Osha Bergman Watanabe & Burton LLP

(57) ABSTRACT

A method of determining an API gravity of a crude oil is provided. The method includes obtaining a reservoir sample containing the crude oil and heating the sample to a first temperature using an oxidative testing apparatus. The sample is then heated to a second temperature, which is greater than the first temperature, over a period using a fixed heating rate. The rate of carbon dioxide emission from the sample is detected during the period of heating to the second temperature. The peak rate of carbon dioxide emission from the sample is then determined and the peak carbon dioxide emission temperature associated with the peak rate of carbon dioxide emission is also determined. The API gravity of the crude oil in the reservoir sample is determined using an empirical correlation between API gravity and the peak carbon dioxide emission temperature associated with the fixed heating rate.

20 Claims, 2 Drawing Sheets

(56) References Cited

U.S. PATENT DOCUMENTS

| | | | |
|---|---|---|---|
| 10,488,327 B2 * | 11/2019 | Thul | ................. G06F 17/14 |
| 2011/0016954 A1 | 1/2011 | Lesieur et al. | |
| 2011/0098936 A1 | 4/2011 | Bats et al. | |
| 2018/0094522 A1 | 4/2018 | van Hal et al. | |
| 2020/0003750 A1 | 1/2020 | Aboussou et al. | |
| 2022/0282605 A1 * | 9/2022 | Ghassal | ............ G01N 33/241 |

FOREIGN PATENT DOCUMENTS

| | | | | |
|---|---|---|---|---|
| CN | 112903900 A * | 6/2021 | | ............ G01N 1/44 |
| RU | 2705942 C1 | 11/2019 | | |
| SU | 1396007 A1 | 5/1988 | | |

OTHER PUBLICATIONS

Beti et al., "A new method of source and reservoir rock pyrolysis to determine the boiling point distribution of petroleum in rock samples," Journal of Petroleum Science and Engineering, Jun. 19, 2018, 10 pages.

International Search Report issued in Corresponding Application No. PCT/US2022/037282, dated Oct. 28, 2022, 4 pages.

Written Opinion issued in Corresponding Application No. PCT/US2022/037282, dated Oct. 28, 2022, 4 pages.

* cited by examiner

OIL API DETERMINATION OF RESERVOIR ROCKS BY OXIDATION

BACKGROUND

Determinations of oil gravities are known to be extremely valuable in the planning required during the development of an oil production prospect. The viscosity and volatility of a crude oil may vary quite widely with variations in API gravity, particularly with respect to gravities within about the 10°-20° API range. For example, in a typical heavy oil prospect, the change in viscosity which accompanies a change of from 11 to 12 degrees in API gravity is approximately 62 centipoises. However, the change in viscosity as the gravity changes from 18 to 19 degrees API is approximately only 3 centipoises. It is important to determine the oil gravity as precisely as possible and as early as possible in the predevelopment economic studies of an oil production prospect.

Some methods of determining the API gravity of an oil include direct measurements on oil samples recovered from production tests or samples obtained by formation fluid-sampling logging devices, or the like, mud-gas chromatographic analyses, and measurements of the refractive index (RI) of oil retorted from cores or samples of the reservoir formation. These types of analysis can be time consuming and require large sample amounts. Pyrolysis approaches in which flame ionization detection is used to determine API gravity have also been demonstrated. However, in such methods require samples to be ground into powders prior to analysis, thus smearing and evaporation may cause sample loss and affect the accuracy of the results.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method of determining an API gravity of a crude oil. The method includes obtaining a reservoir sample containing the crude oil and heating the sample to a first temperature using an oxidative testing apparatus. The sample is then heated to a second temperature over a period using a fixed heating rate using the oxidative testing apparatus. The second temperature is greater than the first temperature. The rate of carbon dioxide emission from the sample is detected during the period of heating to the second temperature. The peak rate of carbon dioxide emission from the sample is then determined and the peak carbon dioxide emission temperature associated with the peak rate of carbon dioxide emission is also determined. The API gravity of the crude oil in the reservoir sample is determined using an empirical correlation between API gravity and the peak carbon dioxide emission temperature associated with the fixed heating rate.

Other aspects and advantages of the claimed subject matter will be apparent from the following description and the appended claims.

DETAILED DESCRIPTION

Embodiments of the present disclosure generally relate to methods of determining API gravity of crude oil in rock samples. API gravity is a critical measure for well planning as it provides information about the type of oil present in portions of a reservoir. In conventional pyrolysis methods used for determining API gravity, samples must be ground into a powder and can result in loss of oil, which may lead to inaccurate results. The methods disclosed herein utilize a relationship between peak $CO_2$ emission and API gravity to readily determine API gravity with no sample grinding.

Figure 1:
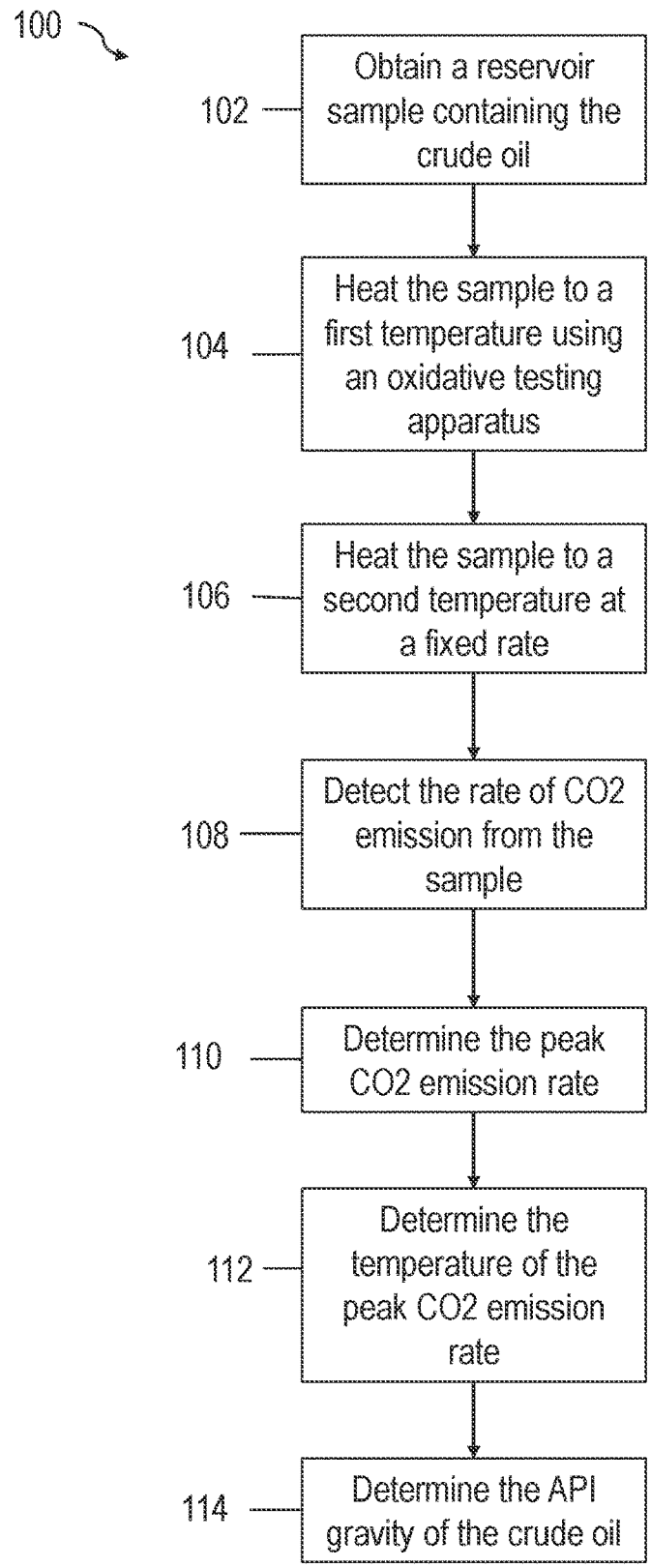
FIG. 1 is a method of determining API gravity in accordance with one or more embodiments.

In one aspect, embodiments disclosed herein relate to a method of determining the API gravity of crude oil. A method in accordance with one or more embodiments is shown in FIG. 1. The method 100 includes obtaining a reservoir sample containing crude oil 102. Then the sample is heated to a first temperature using an oxidative testing apparatus 104. The sample may then be heated at a fixed rate from the first temperature to a second temperature that is greater than the first temperature 106. The rate of $CO_2$ emission is detected throughout the period of heating from the first temperature to the second temperature 108. The highest rate of $CO_2$ emission, referred to as the "peak $CO_2$ emission rate" is then determined 110, and the temperature at which the peak $CO_2$ emission rate occurs is also determined 112. Finally, the API gravity of the crude oil is determined based upon the temperature of the peak $CO_2$ emission rate using an empirical correlation between API gravity and the peak $CO_2$ emission temperature associated with the fixed heating rate 114.

As previously described, embodiment methods include obtaining a reservoir sample containing crude oil 102. The sample may be obtained from any type of reservoir including conventional and unconventional reservoirs, such as sandstone, limestone, shale and carbonate. Samples having very high API values may not be appropriate for the analyses described herein because the oil may evaporate prior to analysis.

In one or more embodiments, the reservoir sample is unprocessed. As used herein, "unprocessed" means that the reservoir sample has not been crushed, ground, powdered, pulverized or otherwise processed prior to use in the disclosed method. Samples may be used directly after being obtained from a reservoir. In some instances, the samples may be mildly cleaned such as by rinsing with water and/or a mild soap to remove debris or other fluids on the outside of the sample. However, other processing is not necessary prior to analysis.

Conventional methods of determining API require that the sample is in a powdered form in order for it to be analyzed. In processing reservoir samples for such analyses, some oil is lost to the grinding process, and more volatile oil may evaporate during processing. Thus, methods disclosed herein may provide more accurate API values due to the fact that unprocessed samples may be used.

The sample may be an appropriate mass for analysis using the oxidative testing apparatus. Enough sample should be used to provide a reasonable signal in the apparatus, however, too much sample may result in saturation of the infrared detector, so an appropriately small amount should be used. Thus, in one or more embodiments, the amount of sample used for the analysis may be from about 20 mg (milligrams) to about 400 mg. The sample amount may be adjusted based upon the oxidative testing apparatus being used and the requirements of the particular apparatus.

After the sample has been obtained, it may be heated to a first temperature using an oxidative testing apparatus 104. As used herein, and "oxidative testing apparatus" is an apparatus configured to heat a sample in the presence of an oxidative atmosphere such as air or oxygen. In one or more embodiments, the oxidative testing apparatus is an oxidation furnace. An example of a suitable oxidation furnace is a RC612 Multiphase Determinator from LECO (Minnesota, USA).] The oxidative testing apparatus may be configured to heat samples at a constant rate under a desired atmosphere. In one or more embodiments, the sample is heated under air. In other embodiments, the sample is heated under oxygen. The oxygen may be supplied to the oxidative testing apparatus at a rate of about 3 L/min (liters per minute) in the disclosed method.

The oxidative testing apparatus in accordance with one or more embodiments may be equipped to measure a number of parameters such as temperature and $CO_2$ emission. In one or more embodiments, the oxidative testing apparatus may be equipped with an infrared (IR) detector which may be used to detect $CO_2$ emission.

As previously described, the sample is heated to a first temperature. In one or more embodiments, the first temperature may be about 400° C. In the samples disclosed herein, minimal oxidation of hydrocarbons takes place at a temperature below 400° C., therefore, minimal $CO_2$ is released from the samples at temperatures below 400° C., so data collected under 400° C. may not provide significant meaningful information.

The sample may then be heated to a second temperature over a period of time using a fixed heating rate. The second temperature may be greater than the first temperature. In one or more embodiments, the second temperature may be about 600° C. Oxidation of hydrocarbons largely takes place between a temperature of 400° C. and 600° C. Above 600° C., some carbonate rocks begin to oxidize, therefore, data collected at temperatures above 600° C. may not provide an accurate reflection of hydrocarbon oxidation.

In one or more embodiments, the sample is heated from the first temperature to the second temperature at a fixed heating rate. As the sample is heated under an oxidizing gas, the hydrocarbons in the sample are oxidized and $CO_2$ is consequently emitted from the sample. The heating rate affects the $CO_2$ emission rate, thus, maintaining a fixed heating rate is important for achieving accurate results. Too fast of a heating rate may result in incomplete oxidation of hydrocarbons and too slow of a heating rate may result in prohibitively long analysis times. In one or more embodiments, the heating rate may be about 25° C./min, about 35° C./min, or about 50° C./min. In particular embodiments, the heating rate is about 35° C./min.

In one or more embodiments, as the sample is heated from the first temperature to the second temperature at a fixed rate, the rate of $CO_2$ emission is detected. As previously described, the $CO_2$ emissions may be detected using an IR detector. The quantity of $CO_2$ emitted from the sample is measured during the period which the sample is heated from the first temperature to the second temperature. An IR detector having a chopper motor may continuously measures the rate of $CO_2$ emission from the sample. In one or more embodiments, the rate of $CO_2$ emission from the sample throughout the heating may be recorded on a computer system coupled to the IR detector to allow for further data analysis.

After the sample has been heated from the first temperature to the second temperature and the $CO_2$ emission has been detected during this period, a peak rate of carbon dioxide emission from the sample during the period is determined. The peak rate of $CO_2$ emission is the highest emission rate measured over the period of time.

The peak $CO_2$ emission rate may then be associated with a temperature, meaning the temperature at which the peak $CO_2$ emission rate occurs is determined for each sample. The temperature of the peak $CO_2$ emission rate may be indicative of the API gravity of the crude oil in the sample. This is because lighter hydrocarbons oxidize faster than heaver hydrocarbons, therefore the peak $CO_2$ emission rate occurs at a lower temperature for lighter hydrocarbons or hydrocarbons having a higher API gravity value. Thus, there exists an inverse relationship between peak $CO_2$ emission temperature and API gravity of the sample.

In one or more embodiments, the API gravity of the crude oil in the reservoir sample may be determined using an empirical correlation between API gravity and the peak $CO_2$ emission temperature associated with the fixed heating rate. An empirical correlation may be predetermined prior to testing samples in accordance with the methods disclosed herein for the heating rate to be used for the testing. For example, in one or more embodiments, prior to analyzing the reservoir sample, a calibration curve may be calculated as the empirical correlation. In such embodiments, different samples having known API gravity values may be analyzed at a given heating rate. In one or more embodiments, at least ten different reference samples with known API gravity values may be analyzed to provide an empirical correlation. The peak $CO_2$ emission temperatures obtained may then be plotted as compared to the known API gravity values. An empirical correlation, such as a linear regression, may then be calculated for a given heating rate. In one or more embodiments, the empirical correlation may be a linear relationship between API gravity and peak $CO_2$ emission temperature.] This empirical correlation may then be used to determine the API gravity from the peak $CO_2$ emission temperature.

The disclosed method may be particularly useful for well planning purposes. For example, determining the API of hydrocarbons in place may help facilitate planning strategies for oil recovery. During drilling operations, API gravity of samples at different depths can be determined in order to avoid oil recovery efforts in very low API gravity zones (indicative of immovable oil). While the porosity and permeability of a reservoir affect what constitutes as immovable oil, in some instances, an API gravity value of less than 15° may be indicative of immovable oil. As such, the methods disclosed herein may be used to determine the productivity of certain regions of a well based on the API gravity of different regions. For example, in one or more embodiments, an API gravity value of at least 20° may be indicative of a good productivity region in which hydrocarbons may be readily recovered. Determining the API gravity can inform decisions regarding the chemical makeup of injectants during enhanced oil recovery processes as oils having certain API gravity values may be amenable to certain chemical recovery methods. Similar to a region of immovable oil, a region having an API value of 15° or less may be amenable to certain enhanced oil recovery methods. The methods disclosed herein may also be used to determine when a well should be abandoned. If no hydrocarbons are detected in the sample, then the well may be plugged and abandoned.

Examples

In order to provide a correlation between peak $CO_2$ emission temperature and API gravity, the API gravity for each sample was determined using POPI (pyrolytic oil-productivity index) analysis. The method for determining POPI may be found in U.S. Pat. No. 6,823,298.

Samples were analyzed in a RC612 Multiphase Determinator from LECO (Minnesota, USA)oxidation furnace equipped with an IR detector.

Tests were performed at heating rates of 25° C., 35° C., and 50° C. for each sample type and data was compiled for each heating rate. A typical sample run was conducted as follows. Samples weighing about 30 to 40 mg were placed in the oxidation furnace and heated to 400° C. under industrial grade oxygen (99.9% purity) at a flow rate of 3 L/min. Then the sample was heated from 400° C. to 600° C. at a rate of 25° C., 35° C. or 50° C., depending upon which set of samples were being run. As the samples were heated at the selected rate, the $CO_2$ emission rate was continuously recorded using software provided with the RC612 Multiphase Determinator instrument. After the $CO_2$ emission rates were recorded from 400° C. to 600° C., the peak $CO_2$ emission temperature was determined by identifying the temperature at which the maximum $CO_2$ emission rate occurred. The peak $CO_2$ emission temperatures were then plotted versus the API gravity value for each sample, and a linear fit was calculated. The results are shown in FIG. 2.

Figure 2:
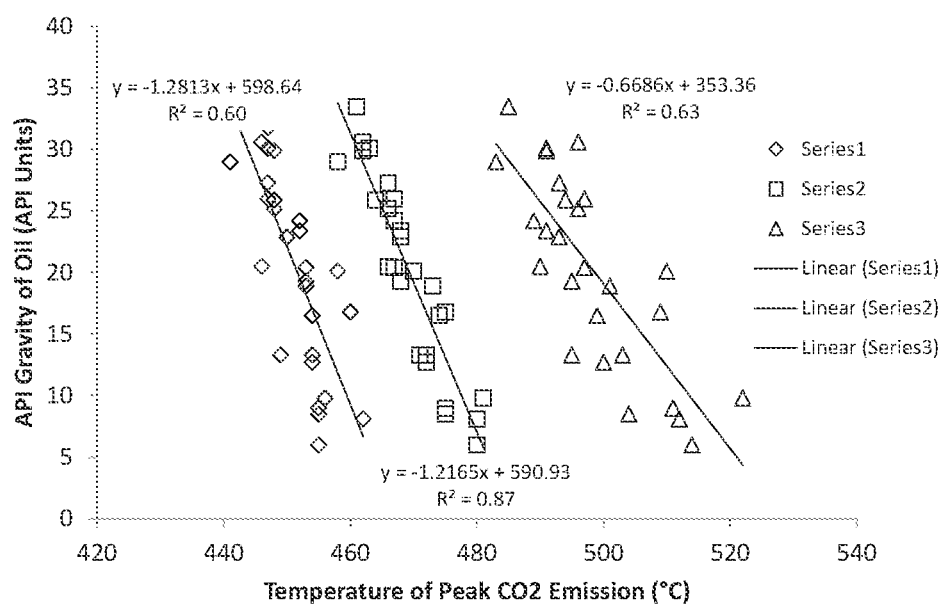
FIG. 2 is a plot of peak $CO_2$ emission data collected for samples in accordance with one or more embodiments.

In FIG. 2, series 1 is data collected at a 25° C. heating rate, series 2 is data collected at a 35° C. heating rate and series 3 is data collected at a 50° C. heating rate. Linear regressions and $R^2$ values were calculated for each series. The $R^2$ values indicate that the 35° C. heating rate provides the strongest correlation (meaning the $R^2$ value is closes to 1).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method of determining an API gravity of a crude oil, comprising:
   obtaining a reservoir sample containing the crude oil;
   heating the sample to a first temperature using an oxidative testing apparatus;
   heating the sample to a second temperature over a period using a fixed heating rate using the oxidative testing apparatus, wherein the second temperature is greater than the first temperature;
   detecting a rate of carbon dioxide emission from the sample during the period of heating to the second temperature;
   determining a peak rate of carbon dioxide emission from the sample during the period;
   determining a peak carbon dioxide emission temperature associated with the peak rate of carbon dioxide emission; and
   determining the API gravity of the crude oil in the reservoir sample using an empirical correlation between API gravity and the peak carbon dioxide emission temperature associated with the fixed heating rate.

2. The method of claim 1 further comprising, prior to obtaining the reservoir sample, calculating a calibration curve as the empirical correlation between the API gravity and the peak carbon dioxide emission temperature associated with the fixed heating rate.

3. The method of claim 2, wherein in the calculating a calibration curve comprises:
   testing at least ten reference samples using the POPI method to obtain API gravity values for each of the reference samples;
   determining the peak rate of carbon dioxide emission for each of the reference samples;
   determining the peak carbon dioxide emission temperature associated with the peak rate of carbon dioxide emission; and
   calculating a linear regression from the API gravity values and the peak carbon dioxide emission temperatures of the reference samples.

4. The method of claim 1, wherein the sample is obtained from a reservoir selected from the group consisting of sandstone, limestone, shale and carbonate.

5. The method of claim 1, wherein the reservoir sample is unprocessed.

6. The method of claim 1, wherein the first temperature is about 400° C.

7. The method of claim 1, wherein the second temperature is about 600° C.

8. The method of claim 1, wherein the heating rate is about 25° C./minute.

9. The method of claim 1, wherein the heating rate is about 35° C./minute.

10. The method of claim 1, wherein the heating rate is about 50° C./minute.

11. The method of claim 1, wherein the rate of carbon dioxide emission is detected using an IR detector.

12. The method of claim 1, comprising flowing oxygen over the sample during the heating from the first temperature to the second temperature.

13. A method of determining productivity of a region of a reservoir, the method comprising:
   obtaining a sample from the region of the reservoir;
   heating the sample to a first temperature using an oxidative testing apparatus;
   heating the sample to a second temperature over a period using a fixed heating rate using the oxidative testing apparatus, wherein the second temperature is greater than the first temperature;
   detecting a rate of carbon dioxide emission from the sample during the period of heating to the second temperature;
   determining a peak rate of carbon dioxide emission from the sample during the period;
   determining a peak carbon dioxide emission temperature associated with the peak rate of carbon dioxide emission;
   determining the API gravity of crude oil in the reservoir sample using an empirical correlation between API gravity and the peak carbon dioxide emission temperature associated with the fixed heating rate; and
   based on the API gravity of the crude oil in the sample, determining the productivity of the region of the reservoir.

14. The method of claim 13, wherein the sample is obtained from a reservoir selected from the group consisting of sandstone, limestone, shale and carbonate.

15. The method of claim 13, wherein the reservoir sample is unprocessed.

16. The method of claim 13, wherein the first temperature is about 400° C.

17. The method of claim 13, wherein the second temperature is about 600° C.

18. The method of claim 13, wherein the heating rate is about 35° C./minute.

19. The method of claim 13, wherein the rate of carbon dioxide emission is detected using an IR detector.

20. The method of claim 13, comprising flowing oxygen over the sample during the heating from the first temperature to the second temperature.

* * * * *